(12) United States Patent
Mueller et al.

(10) Patent No.: US 7,736,628 B2
(45) Date of Patent: Jun. 15, 2010

(54) POWDERED INHALANTS BASED ON MODIFIED LACTOSE MIXTURES AS EXCIPIENT

(75) Inventors: Bernd Wilhelm Mueller, Flintbek (DE); Hartwig Andreas Steckel, Schoenkirchen (DE); Inga-Lis Timmermann, Kiel (DE); Michael Trunk, Ingelheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 182 days.

(21) Appl. No.: 11/232,288

(22) Filed: Sep. 21, 2005

(65) Prior Publication Data

US 2006/0115432 A1 Jun. 1, 2006

(30) Foreign Application Priority Data

Oct. 1, 2004 (DE) .................. 10 2004 048 390

(51) Int. Cl.
*A61K 9/14* (2006.01)
*A61K 31/70* (2006.01)

(52) U.S. Cl. .................. 424/46; 424/489; 424/493; 514/23; 514/54

(58) Field of Classification Search .................. 424/46, 424/489, 493; 514/23, 54
See application file for complete search history.

(56) References Cited

U.S. PATENT DOCUMENTS

| | | | |
|---|---|---|---|
| 3,634,582 | A | 1/1972 | Hartley et al. |
| 5,478,578 | A | 12/1995 | Arnold et al. |
| 7,132,115 | B2 | 11/2006 | Musa et al. |
| 2004/0062719 | A1 * | 4/2004 | Buckton et al. ............ 424/46 |
| 2006/0025326 | A1 * | 2/2006 | Lankinen et al. ............ 514/2 |
| 2006/0120970 | A1 * | 6/2006 | Trunk et al. ............ 424/46 |

FOREIGN PATENT DOCUMENTS

| | | |
|---|---|---|
| WO | WO 92/18110 A1 | 10/1992 |
| WO | WO 95/05805 A1 | 3/1995 |
| WO | WO 00/30265 A3 | 5/2000 |
| WO | WO 01 76560 A1 | 10/2001 |
| WO | WO 02 07705 A1 | 1/2002 |
| WO | WO 0245682 * | 6/2002 |

OTHER PUBLICATIONS

Zeng et al, International Journal of Pharmaceutics 197 (2000) 41-52.*
Newell et al, The use of inverse phase gas chromatography to measure the surface energy of crystalline, amorphous, and recently milled lactose, Pharmaceutical Research, vol. 18, No. 5, 2001.*
Briggner et al, International Journal of Pharmaceutics 105 (1994) 125-135, The use of isothermal microcalorimetry in the study of changes in crystallinity induced during the processing of powders.*
Buckton, Graham et al, "The Use of Gravimetric Studies to Assess the Degree of Crystallinity of Predominantly Crystalline Powders", *International Journal of Pharmaceutics*. Amsterdam: Bd. 123, Nr. 2, 1995, pp. 265-271.
Naini, Venkatesh et al, "Physicochemical Stability of Crystalline Sugars and Their Spray-Dried Forms: Dependence Upon Relative Humidity and Suitability for Use in Powder Inhalers", *Drug Development and Industrial Pharmacy*, New York, New York: US, Bd. 24, Nr. 10, 1998, pp. 895-909.
Dilworth, Sarah E. et al, "Approaches to Determine the Enthalpy of Crystallisation, and Amorphous Content, of Lactose From Isothermal Calorimetric Data", *International Journal of Pharmaceutics*, Amsterdam NL: Bd. 284, Nr. 1-2, Sep. 11, 2004, pp. 83-94.
Steckel, Hartwig et al. "Calorimetric Study on Amorphous Lactose During and After Re-Crystallization at Different Relative Humidity", *Pharmazeutische Industrie*, 2005 Germany: Bd 67, Nr. 6 pp. 709-712.
Hogan, Sarah E., and Graham Buckton. "The Application of Near Infrared Spectroscopy and Dynamic Vapor Sorption to Quantify Low Amorphous Contents of Crystalline Lactose." Pharmaceutical Research vol. 18, No. 1 (2001): 112-116.
Berlin, E., et al. "Calorimetric Measurement of the Heat of Desorption of Water Vapor from Amorphous and Crystalline Lactose." Thermochimica Acta 2 (1971): 143-152.

* cited by examiner

*Primary Examiner*—Mina Haghighatian
(74) *Attorney, Agent, or Firm*—Michael P. Morris; Mary-Ellen M. Devlin; Wendy A. Petka

(57) ABSTRACT

The invention relates to a new process for preparing modified lactose mixtures, these lactose mixtures per se and compositions of medicaments for powder inhalation consisting of one or more micronised active substances and the modified lactose according to the invention.

24 Claims, No Drawings

POWDERED INHALANTS BASED ON MODIFIED LACTOSE MIXTURES AS EXCIPIENT

This application claims priority benefit to German application DE10 2004 048 390, filed Oct. 1, 2004.

The invention relates to a new process for preparing modified lactose mixtures, these lactose mixtures per se and compositions of medicaments for powder inhalation consisting of one or more micronised active substances and the modified lactose according to the invention.

BACKGROUND TO THE INVENTION

Active substances which are to be administered topically by inhalation are usually inhaled orally. If this method proves not to be directly suitable on account of particular qualities of the active substance or special requirements as to its administration, other suitable measures specific to the active substance and excipient must be taken for technical purposes, so that as a function of the physico-chemical properties of the substance a stable product can be produced in an industrially reproducible manner. For substances whose breakdown characteristics in solution prove to be critical, powder inhalation is one option. Not only does the absolute amount of this active substance which has to be administered in one application make particular demands of the formulation, but also the physical stability (e.g. aerodynamic particle size, dispersibility, physico-chemical properties) of the micronised active substance turns out to be a critical prerequisite for the development and manufacture of a powder inhalant.

In the form of powder inhalants, inhalable powders packed into suitable capsules (inhalettes), for example, are delivered using powder inhalers. There are also other known systems in which the quantity of powder to be administered is pre-metered (e.g. blisters), and also multidose powder systems. Alternatively substances may be inhaled by the use of suitable inhalable aerosols in powder form which are suspended, for example, in HFA134a, HFA227 or mixtures thereof as propellant gas.

Usually, powdered inhalants, e.g. in the form of capsules for inhalation, are prepared on the basis of the general teaching as described in DE-A-179 22 07. Another significant aspect in the development of powdered inhalants is that when the active substance is administered by inhalation only particles of a particular aerodynamic size reach the target organ, the lungs. The particle size of these lung-bound particles (inhalable fraction) is in the region of a few μm, typically between 1 and 10 μm, preferably less than 6 μm. Such particles are usually produced by micronisation (e.g. air-jet grinding).

It has become apparent that the optimisation of powdered inhalants, inter alia, can only be achieved by selecting, from the lactoses on the market, the one which is most suitable for the desired product qualities, depending on the characteristics of the active substance. Lactose producers supply a range of qualities depending on the particular requirements, for example. To improve the product qualities of powdered inhalants various possibilities have been suggested in the mean time as to how commercially obtainable lactoses can be modified and tailored to special requirements within the scope of product manufacture (e.g.: DE 4140689).

However, it has also been shown that the morphological and crystalline properties (primarily on the surface of the particles) of the lactose used contribute significantly to the product qualities.

Powdered inhalants as prepared according to the prior art (for example DE-A-179 22 07), in addition to the chemical stability of the active substance and the composition of the medicament as such must above all have physically constant properties. This means specifically that the aerosol properties must remain constant in terms of their aerodunamic characteristics (e.g. aerodynamic particle size). This means that both for the micronised active substance and for the excipients used in the product the latter should be used in their most physico-chemically stable form. For lactose, this means, from a thermodynamic point of view, that this is true when it is in the form of alpha-lactose monohydrate under normal conditions. This is particularly true of the crystalline ordering of the surface of the particles.

It is known that when organic substances are ground, as a result of the significant input of mechanical energy, amorphous fractions may be produced or there may be changes in the crystalline structure leading to thermodynamically less stable modifications. It is also known that lactose may occur in various forms (Coenraad F. Lerk, Physikalisch-pharmazeutische Eigenschaften von Lactose, Pharmazie in unserer Zeit, 16, 1987, No. 2; 39-46).

For example amorphous lactose produced during the grinding of lactose or under other mechanical stress may be recrystallised by known technical methods (e.g. WO 92/18110 or WO 95/05805). However, these methods have the drawback that they only achieve breakdown of amorphous fractions such as occur after micronisation processes. However, these processes do not necessarily result in the breakdown of beta-lactose, which may also occur in these treatment processes, and during the large-scale industrial grinding of lactose to a particle size range with a value of $x_{50}>10$ μm. Thermodynamically unstable fractions such as beta-lactose, for example, even if they are only present on the surface of lactose, constitute a factor which may have a negative effect on the long-term and storage stability of an inhalable powder, for example.

Even after using special methods for recrystallising amorphous fractions of lactose, as described in the prior art (cf e.g. WO 92/18110 or WO 95/05805), particles are obtained which, in spite of recrystallisation of any amorphous fractions present, still show microstructuring on the particles, which can be equated with areas of increased surface energy.

The problem of the present invention is to provide a process by which lactose particles can be modified so that on the one hand (primarily on the surface) they have a highly crystalline texture of the thermodynamically most stable modification under normal conditions, i.e. alpha-lactose monohydrate, and the surfaces of the particles are such that they can be described as being extremely smooth and substantially free of any microstructure.

DESCRIPTION OF THE INVENTION

The method of producing powdered inhalants proposed by the present invention as a solution to the problem mentioned above is based on an at least tertiary mixture which contains, in addition to the one (or more) micronised active substance (s), a carrier lactose and, as third component, a micronised amorphous lactose produced by a spray-drying process, for example. During the process of mixing the premix (the two grades of lactose) the micronised amorphous lactose particles may be added to the carrier lactose by preparing an interactive mixture. By controlled recrystallisation of the amorphous lactose at elevated relative humidity, the surface roughness, unevenness, any fracture edges, pores and energy-activated spots (hot spots) in the carrier lactose may be covered, so as to generate a modified carrier lactose by which the adhesive force between the carrier and the micronised active substance which is to be mixed in a subsequent step can be deliberately reduced and stabilised.

In one aspect the present invention relates to a process for preparing modified lactose mixtures, which is characterised in that in a first step a lactose fraction with a small average particle size of $x_{50}$<50 µm is mixed into a carrier lactose with an average particle size of $x_{50}$ 15 to 80 µm, the lactose fraction with the smaller average particle size containing a high proportion of amorphous lactose, and in a second step the lactose mixture thus obtained is exposed to a relative humidity of at least 80% r.h.

By the median value $X_{50}$ is meant the particle size below which 50% of the quantity of particles lie, measured with a laser diffractometer by the dry dispersion method. This method is known in the art and is disclosed for example in WO 02/30389.

In a preferred embodiment of the process according to the invention the lactose mixture is exposed to the above-mentioned relative humidity for a period of at least 4 hours, preferably at least 6 hours, particularly preferably at least 12 hours, more preferably at least 18 hours.

Within the scope of the process according to the invention the action of moisture is preferably applied at a temperature of above 20° C., particularly preferably in a temperature range from 20-40° C., particularly preferably at 25-35° C., for example at 25° C., 30° C. or 35° C.

In a preferred embodiment of the process according to the invention, the lactose mixture is exposed to a relative humidity of at least 85% r.h., preferably at least 90% r.h., particularly preferably at least 93% r.h.

By the relative humidity (r.h.) is meant, within the scope of the present invention and in accordance with the prior art, the quotient of the partial pressure of the water vapour and the vapour pressure of the water at the temperature in question.

In preferred embodiments of the process according to the invention, moreover, the process is carried out
 a) by preparing the lactose mixture in such a way as to form the largest possible surface area for the powder bed,
 b) then exposing the lactose mixture to the above-mentioned climatic conditions of temperature and humidity;
 c) and then reducing the relative humidity to which the lactose sample is exposed.

Preferably the surface area of the powder bed is only reduced after steps a and b have been carried out. Instead of simply reducing the relative humidity in step c, the relative humidity may for example also be adjusted to a value of less than 20% r.h. or less than 10% r.h. at elevated temperature.

In a possible variant of the process according to the invention the conditioning step may be followed by a drying step in which excess process water is eliminated from the system. Drying may be carried out for example by reducing the relative humidity to less than 20%, preferably less than 15% while increasing the temperature (for example to 70° C., or 75° C. or 80° C. or 85° C.) as a function of a process time of at least 1 h, preferably at least 2 h. In an alternative embodiment the lactose product which is to be dried may also be exposed to an absolutely dry environment, possibly dry nitrogen with a residual moisture content of less than 5% r.h., in which case processing times of at least 6 h, preferably at least 12 h should be selected.

Also particularly preferred is the process mentioned above in which a lactose which is spray-dried by methods known in the art is used in the first step as the lactose with a smaller average particle size and high amorphous content.

Also particularly preferred is the above-mentioned process in which carrier lactose with an average particle size $x_{50}$ of 17 to 50 µm, particularly preferably 20 to 30 µm is used. Also particularly preferred is the above-mentioned process in which the preferably spray-dried lactose with a smaller average particle size has an average particle size $x_{50}$<35 µm, preferably <25 µm. Particularly preferably, this latter lactose has a value $x_{90}$<100 µm, particularly preferably <70 µm.

Also preferred is the process according to the invention in which the amount of preferably spray-dried finer lactose added in the first step makes up 0.1 to 20%, preferably 1 to 15%, particularly preferably 1.5 to 10%, more preferably 2 to 5% of the total amount of excipient.

In another aspect the present invention relates to the lactose mixtures as such which may be obtained by the above method. The present invention also relates to lactose mixtures obtainable by the above method which have a desorption enthalpy of less than 60 J/g, or a desorption enthalpy of less than 40 J/g. The present invention further relates to the use of lactose mixture obtainable by the process according to the invention as an excipient in the production of an inhalable powder containing active substance.

The mixing of the lactose ingredients according to the first step of the process according to the invention and also the mixing of the resulting lactose mixtures with a suitable active substance may be carried out by methods known in the art (e.g. WO 02/30390, WO 03/017970 or WO 03/017979).

The lactose which may be obtained by the manufacturing process according to the invention may be used generally as an excipient for preparing inhalable powders which contain active substances which from a therapeutic point of view should sensibly be administered by inhalation. Preferably active substances are used which are selected for example from among the betamimetics, anticholinergics, corticosteroids, PDEIV-inhibitors, EGFR-inhibitors and LTD4-antagonists or double or triple combinations thereof, such as for example combinations of anticholinergics with betamimetics, corticosteroids, PDEIV-inhibitors, EGFR-inhibitors or LTD4-antagonists, or combinations of betamimetics with corticosteroids, PDEIV-inhibitors, EGFR-inhibitors or LTD4-antagonists, or combinations of corticosteroids with PDEIV-inhibitors, EGFR-inhibitors or LTD4-antagonists or combinations of PDEIV-inhibitors with EGFR-inhibitors or LTD4-antagonists or combinations of EGFR-inhibitors with LTD4-antagonists. The invention also relates to the combinations of three active substances, each selected from one of the above categories of compounds.

Compounds used as betamimetics are preferably selected from among albuterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2 (3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4- methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Preferably the betamimetics are selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Particularly preferred betamimetics are selected from among fenoterol, formoterol, salmeterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1 dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, enantiomers, diastereomers thereof and optionally in the form of the pharmacologically acceptable acid addition salts, solvates or hydrates thereof.

Of these betamimetics, those which are particularly preferred according to the invention are formoterol, salmeterol, 3-(4-{6-[2-hydroxy-2-(4-hydroxy-3-hydroxymethyl-phenyl)-ethylamino]-hexyloxy}-butyl)-benzenesulphonamide, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3- one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 5-[2-(5,6-diethyl-indan-2-ylamino)-1-hydroxy-ethyl]-8-hydroxy-1H-quinolin-2-one, optionally in the form of the racemates, enantiomers, diastereomers thereof and optionally in the form of the pharmacologically acceptable acid addition salts, solvates or hydrates thereof.

According to the invention the preferred acid addition salts of the betamimetics are selected from among hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. Of the above-mentioned acid addition salts, the salts of hydrochloric acid, methanesulphonic acid, benzoic acid and acetic acid are particularly preferred according to the invention.

The anticholinergics used in the process according to the invention are preferably salts selected from among tiotropium salts, oxitropium salts, flutropium salts, ipratropium salts, glycopyrronium salts and trospium salts.

In the above-mentioned salts the cations tiotropium, oxitropium, flutropium, ipratropium, glycopyrronium and trospium are pharmacologically active ingredients. As anions the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodide and methanesulphonate are particularly preferred. Of particular importance is tiotropium bromide. In the case of tiotropium bromide the drug combinations according to the invention preferably contain it in the form of the crystalline tiotropium bromide monohydrate which is known from WO 02/30928. If tiotropium bromide is used in the drug combinations according to the invention in anhydrous form it is preferable to use the anhydrous crystalline tiotropium bromide which is known from WO 03/000265.

The following compounds may preferably also be used as anticholinergics:
tropenol 2,2-diphenylpropionate-methobromide,
scopine 2,2-diphenylpropionate-methobromide,
scopine 2-fluoro-2,2-diphenylacetate-methobromide,
tropenol 2-fluoro-2,2-diphenylacetate-methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, optionally in the form of the solvates or hydrates thereof.

Within the scope of the present invention the term corticosteroids denotes compounds selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6α,9α-difluoro-17α-[(2-furanylcarbonyl)oxy]-11β-hydroxy-16α-methyl-3-oxo-androsta-1,4-diene-17β-carbothionate and (S)-(2-oxo-tetrahydro-furan-3S-yl) 6α,9α-difluoro-11β-hydroxy-16α-methyl-3-oxo-17α-propionyloxy-androsta-1,4-dien-17β-carbothionate, optionally in the form of the racemates, enantiomers or diastereomers and optionally in the form of the salts and derivatives thereof, the solvates and/or hydrates thereof.

Particularly preferred is the steroid selected from among flunisolide, beclomethasone, triamcinolone, budesonide, fluticasone, mometasone, ciclesonide, rofleponide, ST-126, dexamethasone, (S)-fluoromethyl 6α,9α-difluoro-17α-[(2-furanylcarbonyl)oxy]-11β-hydroxy-16α-methyl-3-oxo-androsta-1,4-diene-17β-carbothionate and (S)-(2-oxo-tetrahydro-furan-3S-yl) 6α,9α-difluoro-11β-hydroxy-16α-methyl-3-oxo-17α-propionyloxy-androsta-1,4-diene-17β-carbothionate, optionally in the form of the racemates, enantiomers or diastereomers and optionally in the form of the salts and derivatives thereof, the solvates and/or hydrates thereof.

Particularly preferred is the steroid selected from among budesonide, fluticasone, mometasone, ciclesonide and (S)-fluoromethyl 6α,9α-difluoro-17α-[(2-furanylcarbonyl)oxy]-11β-hydroxy-16α-methyl-3-oxo-androsta-1,4-diene-17β-carbothionate, optionally in the form of the racemates, enantiomers or diastereomers and optionally in the form of the salts and derivatives thereof, the solvates and/or hydrates thereof.

Any reference to steroids includes a reference to any salts or derivatives, hydrates or solvates thereof. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates.

Within the scope of the present invention the term PDEIV-inhibitors denotes compounds selected from among enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropylmethoxybenzamide, NCS-613, pumafentine, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-5-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, CDP840, Bay-198004, D-4418, PD-168787, T-440, T-2585, arofyllin, atizoram, V-11294A, Cl-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferred is the PDE IV-inhibitor selected from among enprofyllin, roflumilast, ariflo (cilomilast), AWD-12-281 (GW-842470), N-(3,5-dichloro-1-oxo-pyridin-4-yl)-4-difluoromethoxy-3-cyclopropylmethoxybenzamide, T-440, T-2585, arofyllin, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], PD-168787, atizoram, V-11294A, Cl-11018, CDC-801, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferred is the PDE IV-inhibitor selected from among roflumilast, ariflo (cilomilast), AWD-12-281 (GW-842470), arofyllin, 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], atizoram, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, of which roflumilast, Z-15370 and AWD-12-281 are of particular importance, optionally in the form of the racemates, enantiomers or diastereomers and optionally in the form of the pharmacologically acceptable acid addition salts, solvates or hydrates thereof.

By acid addition salts with pharmacologically acceptable acids which the above-mentioned PDEIV-inhibitors may optionally be capable of forming are meant, for example, salts selected from among hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Within the scope of the present invention the term LTD4-antagonists denotes compounds selected from among montelukast, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid, pranlukast, zafirlukast, [2-[[2-(4-tert-butyl-2-thiazolyl)-5-benzofuranyl]oxymethyl]phenyl]acetic acid, MCC-847 (ZD-3523), MN-001, MEN-91507 (LM-1507), VUF-5078, VUF-K-8707 and L-733321, optionally in the form of the racemates, enantiomers or diastereomers thereof, optionally in the form of the pharmacologically acceptable acid addition salts as well as optionally in the form of the salts and derivatives thereof, the solvates and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707 and L-733321, optionally in the form of the racemates, enantiomers or diastereomers thereof, optionally in the form of the pharmacologically acceptable acid addition salts as well as optionally in the form of the salts and derivatives thereof, the solvates and/or hydrates thereof.

Particularly preferably the LTD4-antagonist is selected from among montelukast, pranlukast, zafirlukast, MCC-847 (ZD-3523), MN-001 and MEN-91507 (LM-1507), while montelukast, pranlukast and zafirlukast are particularly preferred, optionally in the form of the racemates, enantiomers or diastereomers thereof, optionally in the form of the pharmacologically acceptable acid addition salts as well as optionally in the form of the salts and derivatives thereof, the solvates and/or hydrates thereof.

By acid addition salts with pharmacologically acceptable acids which the above-mentioned LTD4-antagonists may optionally be capable of forming are meant, for example, salts selected from among hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

By salts or derivatives which the above-mentioned LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

Within the scope of the present invention the term EGFR-inhibitors denotes compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2- buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-

6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2.2.1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, cetuximab, trastuzumab, ABX-EGF and Mab ICR-62, optionally in the form of the racemates, enantiomers or diastereomers thereof, optionally in the form of the pharmacologically acceptable acid addition salts, the solvates and/or hydrates thereof.

Preferred EGFR-inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6- oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl) methoxy]-quinazoline, 4-[(3-chloro-4-fluoro-phenyl) amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxy-carbonyl)-piperidin-4-yloxy]-7-methoxy-quinazoline, 4-[(3-chloro-4-fluoro-phenyl)amino]-6-(trans-4-amino-cyclo-hexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl) amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl) carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl) amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl) carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethane-sulphonylamino-cyclohexan-1-yloxy)-7-methoxy-quinazoline, 4-[(3-chloro-4-fluoro-phenyl)amino]-6-(1-methane-sulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl] piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl) amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2.2.1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl) methoxy]-quinazoline, 4-[(3-chloro-4-fluoro-phenyl) amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and cetuximab, optionally in the form of the racemates, enantiomers or diastereomers thereof, optionally in the form of the pharmacologically acceptable acid addition salts, the solvates and/or hydrates thereof.

It is particularly preferable within the scope of the present invention to use those EGFR inhibitors which are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts, the solvates and/or hydrates thereof.

Particularly preferred as EGFR-inhibitors according to the invention are those compounds which are selected from among 4-[(3-chloro-4-fluorophenyl)amino]-6-{[4-(morpholin-4-yl)-1-oxo-2-buten-1-yl]-amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-ethynyl-phenyl)amino]-6,7-bis-(2-methoxy-ethoxy)-quinazoline, 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline,
4-[(3-chloro-4-fluoro-phenyl)amino]-6-{1-[(morpholin-4-yl)carbonyl]-piperidin-4-yl-oxy}-7-methoxy-quinazoline,
4-[(3-chloro-4-fluoro-phenyl)amino]-6-{1-[2-(2-oxopyrrolidin-1-yl)ethyl]-piperidin-4-yloxy}-7-methoxy-quinazoline,
4-[(3-ethynyl-phenyl)amino]-6-(1-acetyl-piperidin-4-yloxy)-7-methoxy-quinazoline,
4-[(3-ethynyl-phenyl)amino]-6-(1-methyl-piperidin-4-yloxy)-7-methoxy-quinazoline,
4-[(3-ethynyl-phenyl)amino]-6-(1-methanesulphonyl-piperidin-4-yloxy)-7-methoxy-quinazoline,
4-[(3-ethynyl-phenyl)amino]-6-{1-[(morpholin-4-yl)carbonyl]-piperidin-4-yloxy}-7-methoxy-quinazoline,
4-[(3-chloro-4-fluoro-phenyl)amino]-6-{1-[(2-methoxyethyl)carbonyl]-piperidin-4-yloxy}-7-methoxy-quinazoline,
4-[(3-chloro-4-fluoro-phenyl)amino]-6-[cis-4-(N-methanesulphonyl-N-methyl-amino)-cyclohexan-1-yloxy]-7-methoxy-quinazoline,
4-[(3-chloro-4-fluoro-phenyl)amino]-6-[cis-4-(N-acetyl-N-methyl-amino)-cyclohexan-1-yloxy]-7-methoxy-quinazoline,
4-[(3-chloro-4-fluoro-phenyl)amino]-6-(trans-4-methylamino-cyclohexan-1-yloxy)-7-methoxy-quinazoline,
4-[(3-chloro-4-fluoro-phenyl)amino]-6-[trans-4-(N-methanesulphonyl-N-methyl-amino)-cyclohexan-1-yloxy]-7-methoxy-quinazoline,
4-[(3-chloro-4-fluoro-phenyl)amino]-6-(trans-4-dimethylamino-cyclohexan-1-yloxy)-7-methoxy-quinazoline,
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline,
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline,
4-[(3-chloro-4-fluoro-phenyl)amino]-6-(1-methanesulphonyl-piperidin-4-yloxy)-7-methoxy-quinazoline and
4-[(3-chloro-4-fluoro-phenyl)amino]-6-(1-cyano-piperidin-4-yloxy)-7-methoxy-quinazoline, optionally in the form of the racemates, enantiomers or diastereomers thereof, optionally in the form of the pharmacologically acceptable acid addition salts, the solvates and/or hydrates thereof.

By acid addition salts with pharmacologically acceptable acids which the above-mentioned EGFR-inhibitors may optionally be capable of forming are meant, for example, salts selected from among hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Surprisingly it has been found that powdered inhalants which contain as excipient lactose, obtained by the process according to the invention, not only have an elevated inhalable fraction, but, in particular, formulations based on this invention also have enhanced "robustness".

The present invention therefore also relates to inhalable powders which contain as excipient, in addition to one or more of the above-mentioned active substances, the lactose mixture which may be obtained according to the invention.

Moreover the present invention relates to the use of the lactose obtained by the process according to the invention for preparing a pharmaceutical composition for the treatment of ailments in which the administration by inhalation of medicaments containing active substance may provide a therapeutic benefit. Moreover the present invention relates to the use of the lactose mixture obtainable by the process according to the invention for preparing an inhalable powder containing an active substance.

The invention claimed is:

1. A process for preparing modified lactose mixtures, the process comprising:
    mixing a lactose fraction with a small average particle size of $x_{50}$<50 μm into a carrier lactose with an average particle size of $x_{50}$ being from 15 μm to 80 μm to form a lactose mixture, wherein the lactose fraction with the small average particle size contains amorphous lactose;
    exposing the lactose mixture to a relative humidity (r.h.) of at least 85% r.h. at a temperature in the range from 20 to 40° C. for a period of at least 4 hours; and
    exposing the lactose mixture to a relative humidity (r.h.) of less than 20% r.h. for a period of at least 1 hour while increasing the temperature to 70° C., so that a modified lactose mixture of lactose particles having crystalline alpha-lactose-monohydrate surfaces is produced.

2. The process according to claim 1, wherein the lactose mixture is spread out to form a powder bed, the powder bed being formed in such a way as to form the largest possible surface area for the powder bed, and, upon exposing the lactose mixture formed in the powder bed to a relative humidity of at least 80% r.h. for a selected temperature and a selected time period, the relative humidity to which the lactose sample is exposed is reduced.

3. A lactose mixture of lactose particles having crystalline alpha-lactose-monohydrate surfaces, wherein the lactose mixture comprises a lactose fraction with an average particle size $x_{50}$<50 μm and a carrier lactose with an average particle size $x_{50}$ from 15 μm to 80 μm, which is formed by the process according to claim 1, wherein the lactose mixture has a desorption enthalpy of less than 60 J/g.

4. The lactose mixture according to claim 3, characterised in that it has a desorption enthalpy of less than 40 J/g.

5. A method for preparing an inhalable powder containing active substance, the method comprising:
    forming the modified lactose mixture by mixing a lactose fraction with a small average particle size of $x_{50}$<50 μm into a carrier lactose with an average particle size of $x_{50}$ being from 15 μm to 80 μm to form a lactose mixture, wherein the lactose fraction with the small average particle size contains amorphous lactose;
    exposing the lactose mixture to a relative humidity (r.h.) of at least 85% r.h. at a temperature in the range from 20 to 40° C. for a period of at least 4 hours; and
    exposing the lactose mixture to a relative humidity (r.h.) of less than 20% r.h. for a period of at least 1 hour while increasing the temperature to 70° C., so that a modified lactose mixture of lactose particles having crystalline alpha-lactose-monohydrate surfaces and a desorption enthalpy of less than 60 J/g is produced; and
    combining the modified lactose mixture with an active substance.

6. An Inhalable powder comprising at least one active substance, an excipient and the lactose mixture according to claim 3.

7. The Inhalable powder according to claim 6, wherein the at least one active substance is selected from the group consisting of betamimetics, anticholinergics, corticosteroids, PDEIV-inhibitors, EGFR-inhibitors, LTD4-antagonists, and combinations thereof.

8. The process according to claim 1, wherein the relative humidity of at least 85% r.h. is a relative humidity of at least 90% r.h.

9. The process according to claim 1, wherein the lactose mixture is exposed to the relative humidity of at least 85% r.h. at a temperature in the range from 25 to 35° C.

10. The process according to claim 5, wherein the lactose mixture is exposed to the relative humidity of at least 85% at a temperature in the range from 25 to 35° C.

11. The process according to claim 1, wherein the relative humidity of at least 85% r.h. is a relative humidity of at least 93% r.h.

12. A process for preparing modified lactose mixtures, the process comprising:
mixing a lactose fraction with a small average particle size $x_{50}$<25 µm into a carrier lactose with an average particle size $x_{50}$ of 17 µm to 50 µm to form a lactose mixture, wherein the lactose fraction with the small average particle size contains amorphous lactose, and wherein the lactose mixture contains 1.5 to 10% of the lactose fraction with the small average particle size;
exposing the lactose mixture to a relative humidity of at least 85% r.h. at a temperature in the range from 25 to 35° C. for a period of at least 4 hours; and
exposing the lactose mixture to a relative humidity (r.h.) of less than 20% r.h. for a period of at least 1 hour while increasing the temperature to 70° C., so that a modified lactose mixture of lactose particles having crystalline alpha-lactose-monohydrate surfaces and a desorption enthalpy of less than 60 J/g is produced.

13. The process according to claim 5, wherein the relative humidity of at least 85% r.h. is a relative humidity of at least 90% r.h.

14. The process according to claim 5, wherein the relative humidity of at least 85% r.h. is a relative humidity of at least 93% r.h.

15. The process according to claim 12, wherein the relative humidity of at least 85% r.h. is a relative humidity of at least 90% r.h.

16. The process according to claim 1, wherein the lactose mixture is exposed to the relative humidity of less than 20% while increasing the temperature to 75° C.

17. The process according to claim 1, wherein the lactose mixture is exposed to the relative humidity of less than 20% while increasing the temperature to 80° C.

18. The process according to claim 1, wherein the lactose mixture is exposed to the relative humidity of less than 20% while increasing the temperature to 85° C.

19. The process according to claim 5, wherein the lactose mixture is exposed to the relative humidity of less than 20% while increasing the temperature to 75° C.

20. The process according to claim 5, wherein the lactose mixture is exposed to the relative humidity of less than 20% while increasing the temperature to 80° C.

21. The process according to claim 5, wherein the lactose mixture is exposed to the relative humidity of less than 20% while increasing the temperature to 85° C.

22. The process according to claim 12, wherein the lactose mixture is exposed to the relative humidity of less than 20% while increasing the temperature to 75° C.

23. The process according to claim 12, wherein the lactose mixture is exposed to the relative humidity of less than 20% while increasing the temperature to 80° C.

24. The process according to claim 12, wherein the lactose mixture is exposed to the relative humidity of less than 20% while increasing the temperature to 85° C.

* * * * *